(12) United States Patent
Hiraoka

(10) Patent No.: US 9,155,526 B2
(45) Date of Patent: Oct. 13, 2015

(54) PUNCTURE APPARATUS WITH AUTOMATIC PUNCTURE FUNCTION

(75) Inventor: Jin Hiraoka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 1348 days.

(21) Appl. No.: 11/846,934

(22) Filed: Aug. 29, 2007

(65) Prior Publication Data

US 2009/0062830 A1 Mar. 5, 2009

(51) Int. Cl.
*A61B 17/34* (2006.01)
*A61B 10/02* (2006.01)
(Continued)

(52) U.S. Cl.
CPC .......... *A61B 10/0233* (2013.01); *A61B 10/0283* (2013.01); *A61B 2010/0208* (2013.01); *A61B 2010/045* (2013.01); *A61B 2017/3443* (2013.01); *A61B 2019/4805* (2013.01)

(58) Field of Classification Search
CPC .......... A61B 10/0233; A61B 10/0283; A61B 2010/045; A61B 2017/3443; A61B 2019/4805
USPC ................................................. 606/185, 167
See application file for complete search history.

(56) References Cited

U.S. PATENT DOCUMENTS 5,356,420 A * 10/1994 Czernecki et al. ............. 606/182
5,551,442 A * 9/1996 Kanner et al. ................. 600/567

(Continued)

FOREIGN PATENT DOCUMENTS

EP 1075850 A2 2/2001
EP 1 923 003 A1 5/2008
(Continued)

OTHER PUBLICATIONS

Notice of Allowance dated Feb. 19, 2013 from corresponding Japanese Patent Application 2008-214332 together with an English language translation.
(Continued)

*Primary Examiner* — Kathleen Holwerda
*Assistant Examiner* — Sarah Simpson
(74) *Attorney, Agent, or Firm* — Scully, Scott, Murphy & Presser, PC

(57) ABSTRACT

The present invention is a puncture apparatus with an automatic puncture function, that includes: a hollow needle tube; a flexible sheath having the needle tube inserted therethrough; a main body having one of the ends of the sheath fixed thereto; a slider attached to the main body, the slider being capable of sliding in an axial direction relative to the main body; a needle tube-maneuvering section, attached to the slider, capable of sliding in an axial direction relative to the slider, the needle tube-maneuvering section having an end section of the needle tube fixed thereto; a retraction state-maintaining member for maintaining the needle tube-maneuvering section in the retracted state toward a proximal end; an urging member, provided in the needle tube-maneuvering section, for urging a retracted state of the needle tube-maneuvering section toward the distal end; an operation section for resetting the operation of the retraction state-maintaining member; releasing the ejection force; and projecting the needle tube-maneuvering section toward the distal end; and an unintentional operation preventive member, provided to the slider, for holding the operation section in an non-operating state, wherein the non-operating state of the operation section held by the unintentional operation preventive member can be reset only when the distal end of the needle tube is exposed by sliding the slider to a predetermined position relative to the main body.

8 Claims, 19 Drawing Sheets

(51) Int. Cl.
*A61B 10/04* (2006.01)
*A61B 19/00* (2006.01)

(56) References Cited

U.S. PATENT DOCUMENTS

| | | | |
|---|---|---|---|
| 5,702,344 A | | 12/1997 | Silverstein |
| 5,741,288 A | * | 4/1998 | Rife .............................. 606/181 |
| 2008/0306334 A1 | * | 12/2008 | Okada ........................... 600/104 |
| 2009/0264794 A1 | * | 10/2009 | Kodama ........................ 600/567 |

FOREIGN PATENT DOCUMENTS

| | | |
|---|---|---|
| JP | H7-143992 A | 6/1995 |
| JP | H7-222735 A | 8/1995 |
| JP | H9-75351 A | 3/1997 |
| JP | H11-503643 A | 3/1999 |
| JP | 11-506634 | 6/1999 |
| JP | 2001-37765 A | 2/2001 |
| JP | 2001-120557 | 5/2001 |
| JP | 2007-68732 | 3/2007 |
| JP | WO 2007/029713 * 3/2007 ............... A61B 1/00 |
| WO | 96/32981 A1 | 10/1996 |
| WO | WO 03/026509 A2 | 4/2003 |
| WO | 2005/102434 A2 | 11/2005 |

OTHER PUBLICATIONS

European Search Report dated Jul. 27, 2011 for corresponding European Application No. 11 00 3020.2.

* cited by examiner

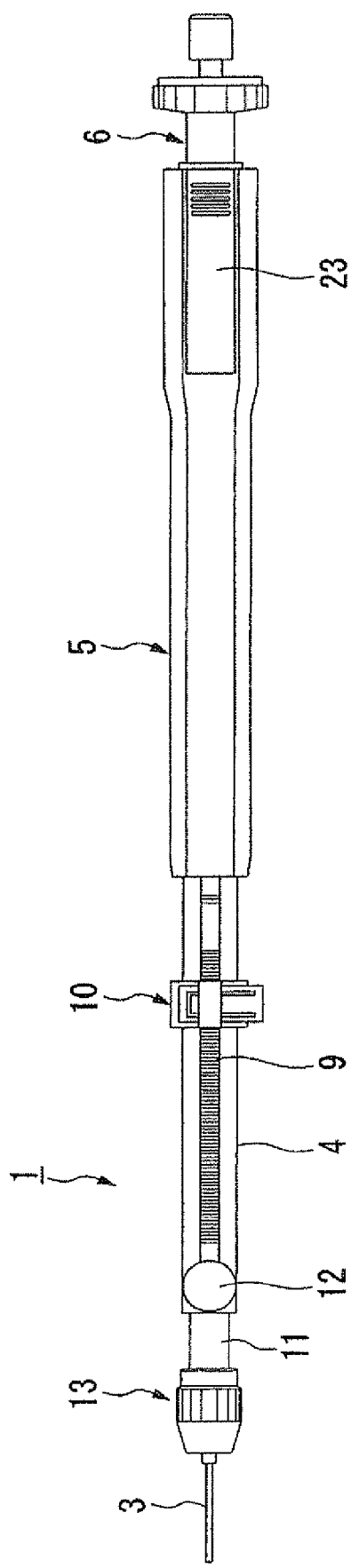

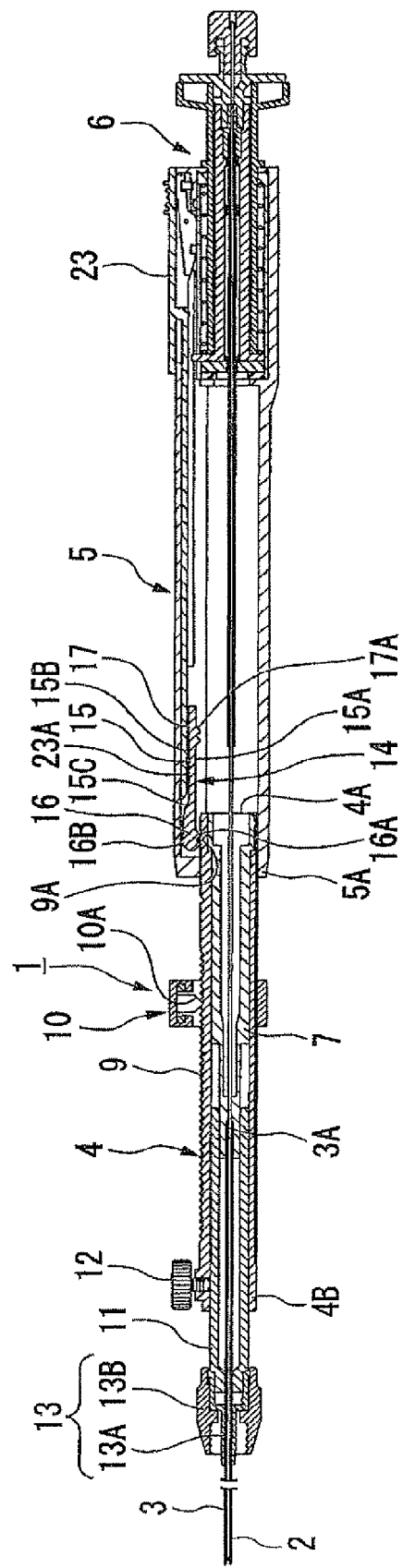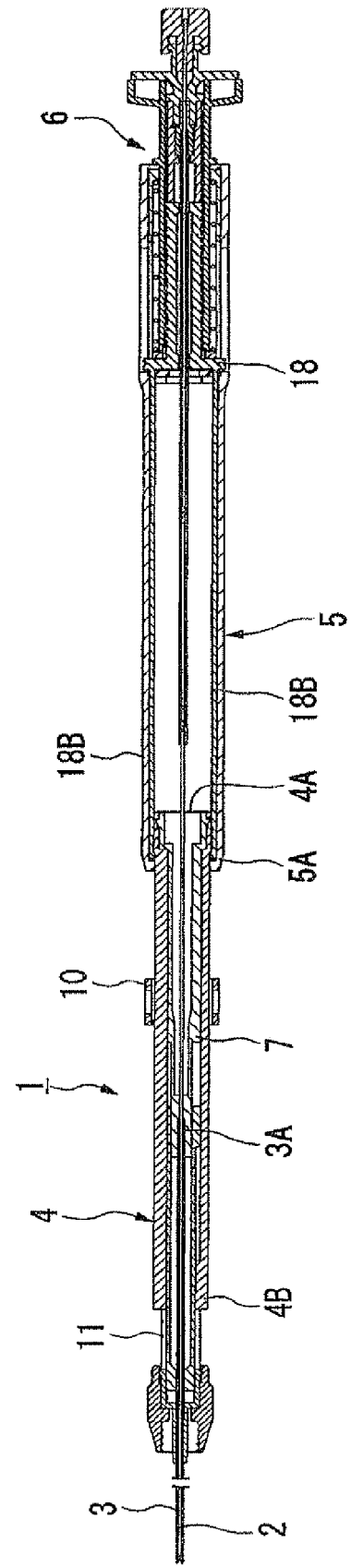

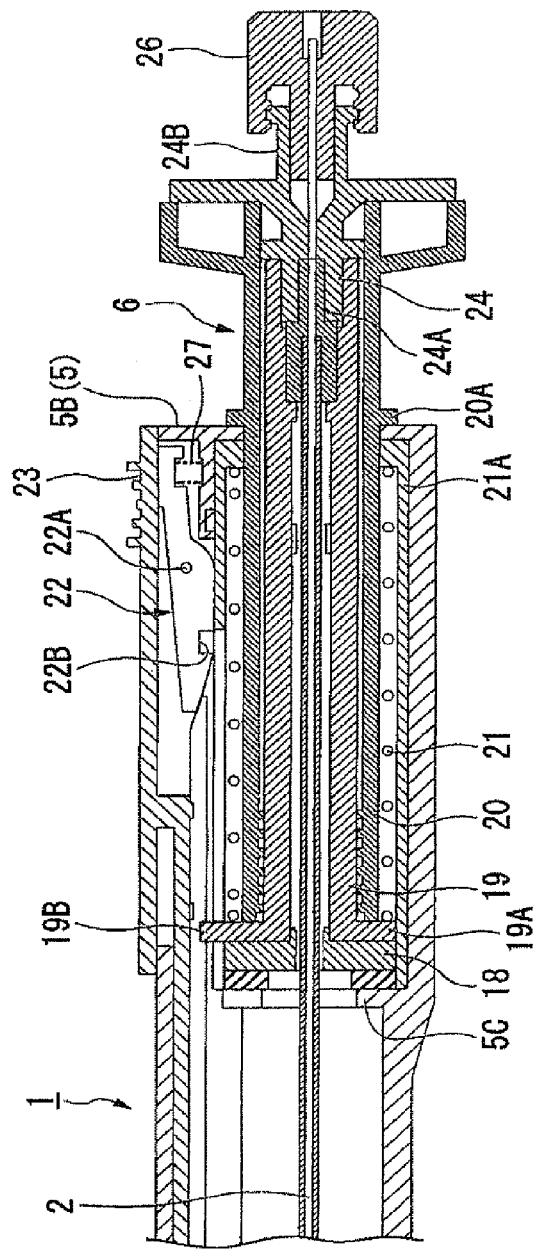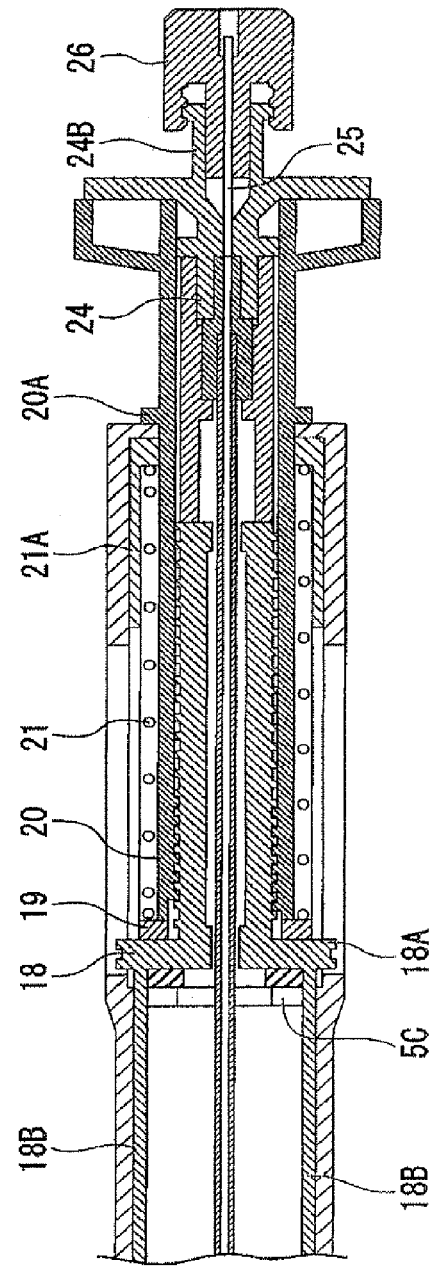

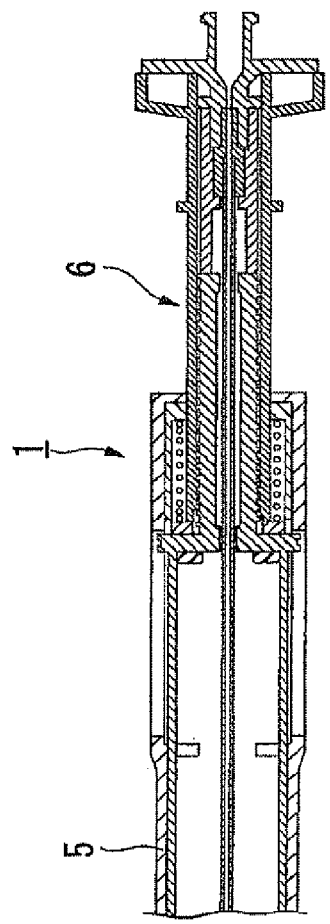
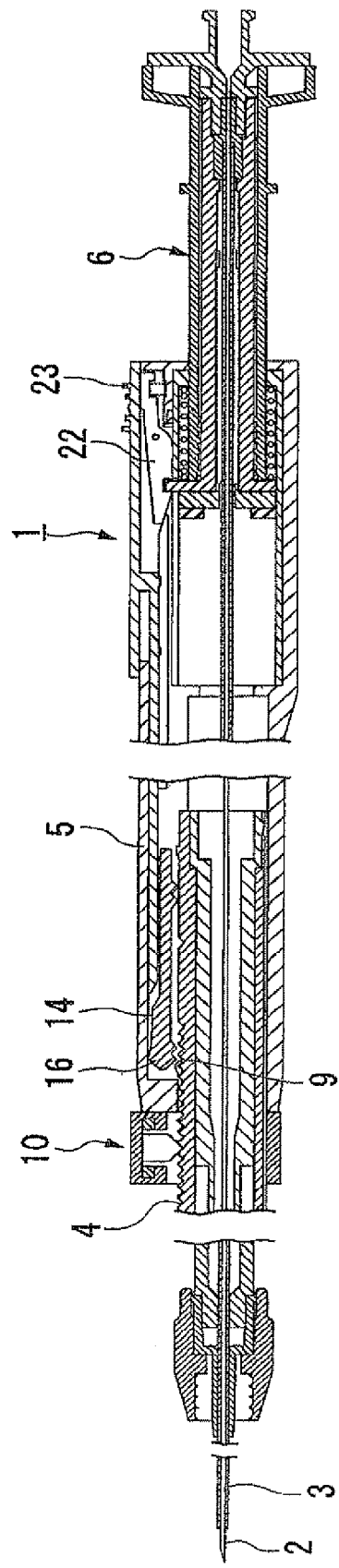
FIG. 5A
FIG. 5B

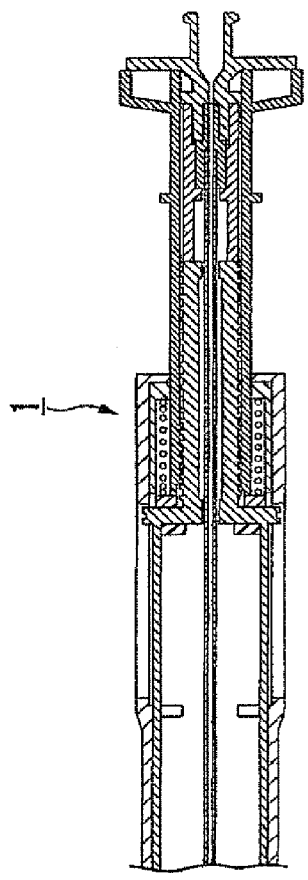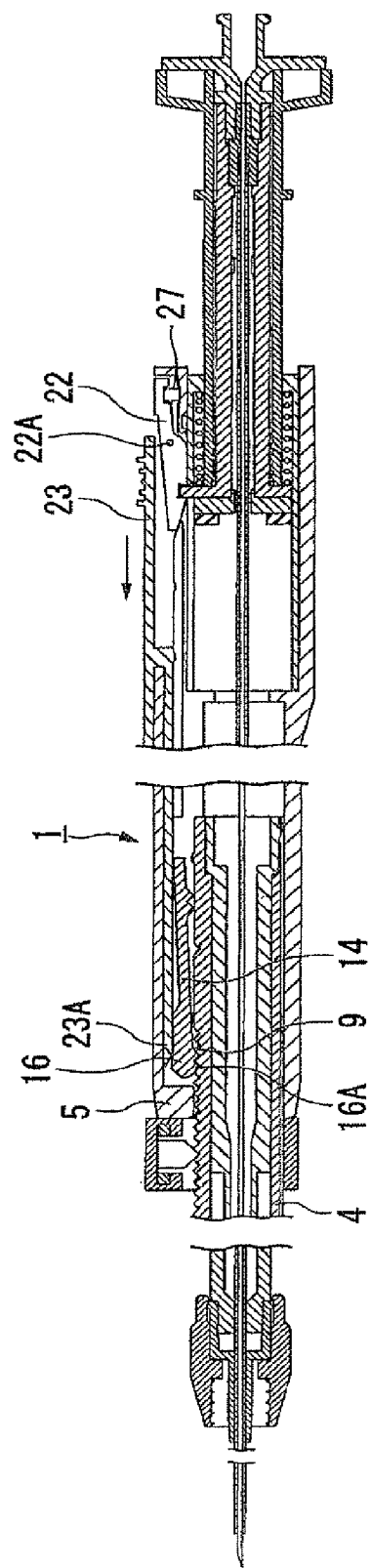
FIG. 7A
FIG. 7B

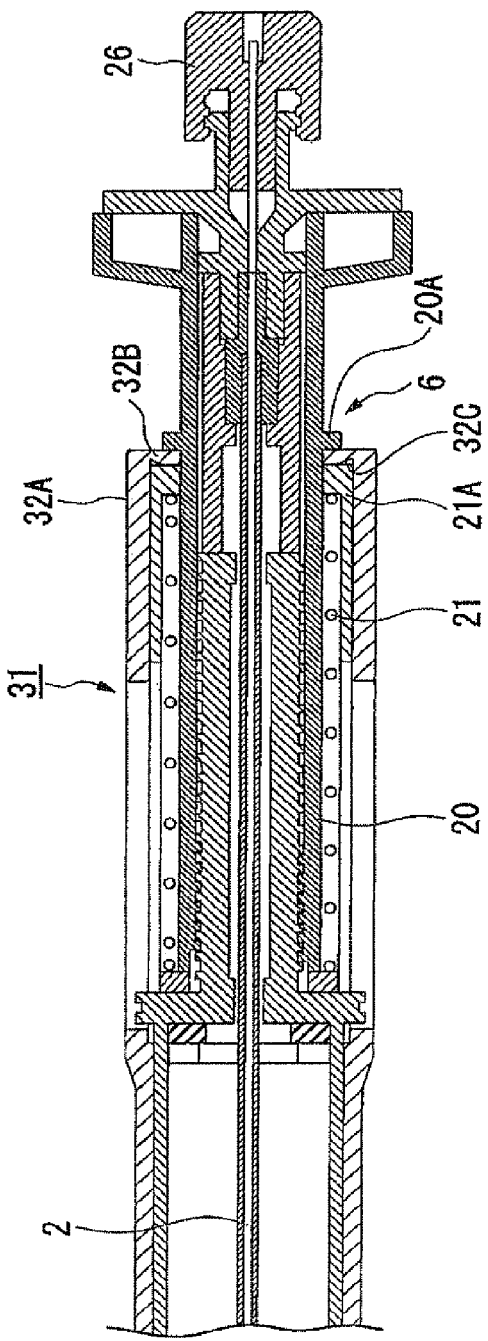
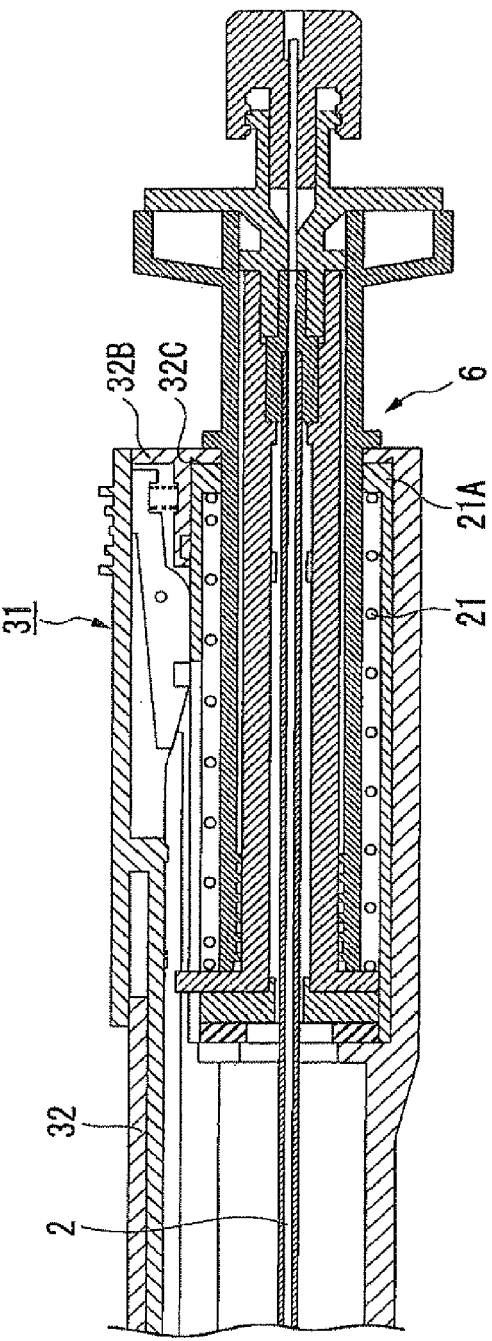

PUNCTURE APPARATUS WITH AUTOMATIC PUNCTURE FUNCTION

BACKGROUND OF THE INVENTION

1. Field of the Invention

The present invention relates to a puncture apparatus having an automatic puncture function used for endoscopic insertion.

2. Background Art

In conventionally known puncture apparatuses having automatic puncture function using a hollow needle for removing tissue for autopsy, high speed movement of the needle provided by accumulating an ejection force in an automatic puncture mechanism having a spring, etc. and discharging the accumulated force all at once to enable automatic puncture in a case where puncture to a stiffened object tissue is difficult due to fibrosis.

The object tissue may be damaged if the automatic puncture mechanism providing high speed and powerful puncture is unintentionally activated. Known puncture apparatuses proposed for preventing this are provided with a protection cover that covers an operation switch for activating the automatic puncture mechanism (for example, Japanese Unexamined Patent Application, First Publication No. 2007-68732).

However, the operation switch can be exposed by opening the protection cover prior to a manual puncture of the puncture apparatus disclosed by the Japanese Unexamined Patent Application, First Publication No. 2007-68732. Therefore, an unintentional activation of the automatic puncture function cannot be prevented if an endoscopist conducts therapeutic operation while opening the protection cover.

SUMMARY OF THE INVENTION

The present invention was made in consideration of the aforementioned circumstances, and an object of the present invention is to provide a puncture apparatus with an automatic puncture function that can prevent an erroneous automatic puncture reliably.

A first aspect of the present invention is a puncture apparatus with an automatic puncture function, that includes: a hollow needle tube; a flexible sheath having the needle tube inserted therethrough; a main body having one of the ends of the sheath fixed thereto; a slider attached to one of the ends of the main body, the slider being capable of sliding in an axial direction relative to the main body; a needle tube-maneuvering section, attached to one of the ends of the slider, capable of sliding in an axial direction relative to the slider, the needle tube-maneuvering section having all end section of the needle tube fixed thereto; a retraction state-maintaining member for maintaining the needle tube-maneuvering section in a retracted state toward a proximal end; an ejecting member provided in the needle tube-maneuvering section, an ejection force for projecting the needle tube-maneuvering section toward the distal end being accumulated in the needle tube-maneuvering section retracted toward the proximal end; an operation section for resetting the operation of the retraction state-maintaining member, releasing the ejection force, and projecting the needle tube-maneuvering section toward the distal end; and an unintentional operation preventive member, provided to the slider, for holding the operation section in a non-operating state, wherein the non-operating state of the operation section held by the unintentional operation preventive member can be reset only when the distal end of the needle tube is exposed by sliding the slider to a predetermined position relative to the main body.

It may be configured so that: the main body has a main body engagement section on an outer periphery; the slider has an engagement member having an engagement projection at a first end section, the engagement projection can engage with the main body engagement section; one of the end sections of the unintentional operation preventive member enters between the engagement member and the slider; a correlation is obtained in which the main body engagement section can engage with the engagement projection when the distal end of the needle tube is exposed by sliding the slider to the predetermined position relative to the main body, the unintentional operation preventive member can slide in the axial direction; and the non-operating state of the operation section held by the unintentional operation preventive member can be reset.

It may be configured so that: the unintentional operation preventive member is a protection cover that covers the operation section; and the operation section can be operably exposed by retracting the protection cover only when the distal end of the needle tube is exposed from the sheath by sliding the slider to the predetermined position relative to the main body.

It may be configured so that: the unintentional operation preventive member is an interposed member that is interposed between the operation section and the slider; and the operation section can be operably exposed by retracting the interposed member only when the distal end of the needle tube is exposed from the sheath by sliding the slider toward the predetermined position relative to the main body.

It may be configured so that the main body engagement section is a rack of teeth each having a tilting surface being at an angle of 45 degrees or steeper relative to the axial line of the main body.

A second aspect of the present invention is a puncture apparatus with an automatic puncture function, that includes: an automatic puncture unit; and an unintentional operation preventive member, wherein the automatic puncture unit comprises: a hollow needle tube; a flexible sheath having the needle tube inserted therethrough; a main body having one of the ends of the sheath fixed thereto; a slider attached to one of the ends of the main body, the slider being capable of sliding in an axial direction relative to the main body; a needle tube-maneuvering section, attached to one of the ends of the slider, capable of sliding in an axial direction relative to the slider, the needle tube-maneuvering section having an end section of the needle tube fixed thereto; a retraction state-maintaining member for maintaining the needle tube-maneuvering section in a retracted state toward a proximal end; an ejecting member provided in the needle tube-maneuvering section, an ejection force for projecting the needle tube-maneuvering section toward the distal end being accumulated in the needle tube-maneuvering section retracted toward the proximal end, the ejecting member pressed between a front end of the needle tube-maneuvering section and a rear end of the slider; and an operation section for releasing the ejection force by resetting the needle tube-maneuvering section held by the retraction state-maintaining member and for projecting the needle tube-maneuvering section toward the distal end, wherein the needle tube-maneuvering section is provided to the slider, for holding the operation section in a non-operating state, and wherein the ejection force is released when the rear end of the operation switch 73 is destroyed by applying a specific value of load or greater to the automatic puncture unit.

A third aspect of the present invention is a puncture apparatus with an automatic puncture function, that includes: a hollow needle tube; a flexible sheath having the needle tube inserted therethrough; a main body having one of the ends of the sheath fixed thereto; a first slider attached to one of the ends of the main body, the first slider being capable of sliding in an axial direction relative to the main body, the sheath being inserted through the first slider; a second slider attached to a second end section of the main body, the second slider being capable of sliding in the axial direction relative to the main body; a needle tube-maneuvering section, attached to one of the ends of the second slider, capable of sliding in the axial direction relative to the second slider, the needle tube-maneuvering section having an end section of the needle tube fixed thereto; a retraction state-maintaining member for maintaining the needle tube-maneuvering section in a retracted state toward a proximal end; an ejecting member provided in the needle tube-maneuvering section, an ejection force for projecting the needle tube-maneuvering section toward the distal end being accumulated in the retracted state of needle tube-maneuvering section retracted toward the proximal end; an operation section for releasing the ejection force by resetting the needle tube-maneuvering section held by the retraction state-maintaining member and for projecting the needle tube-maneuvering section toward the distal end; and an unintentional operation preventive member, provided to the second slider, for holding the operation section in an non-operating state, wherein the first slider has a plurality of sections to be fixed, the main body has a slider-fixing section that can be engaged with the sections to be fixed, and a predetermined and fixed correlation between the first slider and the main body is obtained by engaging the sections to be fixed with the slider-fixing section.

It may be configured so that the section to be attached is a rack of teeth each having a tilting surface being at an angle of 45 degrees or steeper relative to the axial line of the main body.

A fourth aspect of the present invention is a puncture apparatus with an automatic puncture function, comprising: a hollow needle tube; a flexible sheath having the needle tube inserted therethrough; a main body having one of the ends of the sheath fixed thereto; a slider attached to one of the ends of the main body, the slider being capable of sliding in an axial direction relative to the main body; a needle tube-maneuvering section, attached to one of the ends of the slider, capable of sliding in an axial direction relative to the slider, the needle tube-maneuvering section having an end section of the needle tube fixed thereto; a retraction state-maintaining member for maintaining the needle tube-maneuvering section in a retracted state toward a proximal end; an ejecting member provided in the needle tube-maneuvering section, for accumulating an ejection force for projecting the needle tube-maneuvering section toward the distal end in a state where the needle tube-maneuvering section is retracted toward the proximal end; an operation section for releasing the ejection force by resetting the needle tube-maneuvering section held by the retraction state-maintaining member and for projecting the needle tube-maneuvering section toward the distal end; an unintentional operation preventive member, provided to the slider, for holding the operation section in a non-operating state; a locking section provided to an end section of the main body; and an engagement member, provided to the slider, having a plurality of engagement projections, wherein when the needle tube-maneuvering section is held by the retraction state-maintaining member in a retracted state, and when the distal end of the needle tube is exposed from the sheath by sliding the slider to a predetermined position relative to the main body, the locking section engages with the engagement projections so that the slider engages with the main body and so that the slider can be slid manually relative to the main body.

BRIEF DESCRIPTION OF DRAWINGS

FIG. 1A is a plan view of a puncture apparatus according to a first embodiment of the present invention. FIG. 1B is a front view of a handling portion of the puncture apparatus.

FIG. 2A is a vertical cross-section of the puncture apparatus. FIG. 2B is a horizontal cross-section of the puncture apparatus.

FIG. 3A is an enlarged view of an automatic puncture unit and the area around, and FIG. 3B is an enlarged view of the automatic puncture unit shown in FIG. 2B.

FIG. 5A is a horizontal cross-section of a manual puncture state of the automatic puncture unit of the puncture apparatus. FIG. 5B is a vertical cross-section of the same state.

FIG. 7A is a horizontal cross-section of a slid stated of the protection cover of the puncture apparatus. FIG. 7B is a vertical cross-section of the same state.

FIG. 9A is an enlarged horizontal cross-section of am automatic picture unit 6 of the puncture apparatus and the area therearound according to a second embodiment of the present invention. FIG. 9B is an enlarged vertical cross-section thereof.

DETAILED DESCRIPTION OF THE INVENTION

Figure 4A:
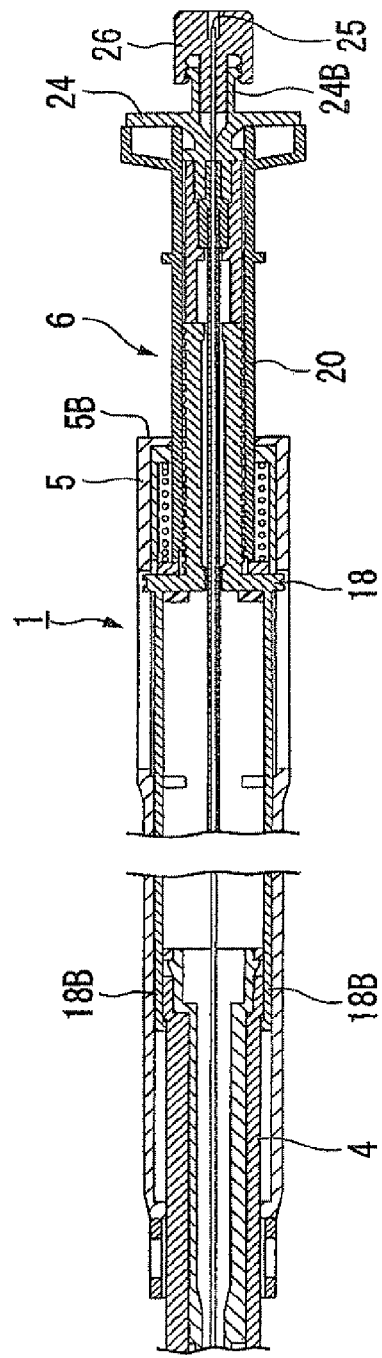
FIG. 4A is a horizontal cross-section of a loading state of the automatic puncture unit of the puncture apparatus.

A puncture apparatus with automatic puncture function according to a first embodiment of the present invention is explained as follows with reference to FIGS. 1A to 8B.

FIG. 1A is a plan view of a puncture apparatus (puncture apparatus with automatic puncture function) 1 according to a first embodiment of the present invention. FIG. 1B is a front view of a handling portion of the puncture apparatus 1. Also, FIG. 2A is a vertical cross-section of the puncture apparatus 1, and FIG. 2B is a horizontal cross-section of the puncture apparatus 1. As illustrated in FIGS. 1A to 2B, the puncture apparatus 1 includes: a hollow needle tube 2 for removing tissue for autopsy; a sheath 3 having the needle tube 2 inserted therein; a main body 4 having an end of the sheath 3 fixed thereto; a slider (second slider) 5 attached to the main body 4; and an automatic puncture unit 6 attached to the slider 5.

The needle tube 2 is a metal hollow member having a certain flexibility. The needle tube 2 used for puncturing a pancreas and a removal therefrom takes a rodlike tissue for autopsy thereinto.

The sheath 3, which is a resin-made tubular member having flexibility, has the needle tube 2 therethrough as illustrated in FIGS. 2A and 2B.

The main body 4 is a resin-made cylindrical member. The sheath 3 is inserted through the main body 4 and fixed to a sheath-fixing member 7 attached in the main body 4. The needle tube 2 inserted through a protection pipe, not shown in the drawings, extends along the slider 5.

Rack teeth (main body engagement section) 9 are provided on an outer periphery of the main body 4 along an axial direction. Attached on the rack teeth 9 is a needle adjuster 10 having an engagement section 10A that engages with the rack teeth 9 at an arbitrary position thereon. The needle adjuster 10 is used for adjusting the length of the needle tube 2 from the distal end of the sheath 3 as explained later. An engagement projection section (engagement section) 9A having substantially a trapezoid shape is provided in the vicinity of a first end section 4A of the main body 4 on a line extending from the rack teeth 9. Functions of the engagement projection section 9A are explained later.

A sheath adjuster (first slider) 11 for adjusting the length of the sheath 3 in an endoscope is inserted through a second end section 4B of the main body 4 located at the distal end of the needle tube 2. The sheath adjuster 11 is capable of sliding in a specific range in an axial direction of the main body 4. The sheath and the needle tube 2 are inserted through the sheath adjuster 11. The sheath adjuster 11 can be fixed at an arbitrary position relative to the main body 4 by screwing the sheath adjuster screw 12 attached to the second end section 4B of the main body 4 into the sheath adjuster 11.

A section 13 to be attached with an endoscope is provided at the distal end of the sheath adjuster 11. The puncture apparatus 1 is attached to a forceps port at the section 13. The section 13 includes a scope cap 13A fixed to the distal end of the sheath adjuster 11 and a cap screw 13B attached rotatably around an axial line of the scope cap 13A. A screw thread is formed on an inner surface of the cap screw 13B. An operation switch 22, which will be explained later, can be moved to a position that facilitates a user to operate by rotating the main body 4 or a slider 5 after the puncture apparatus 1 is attached to the forceps port of the endoscope since the cap screw 13B can be rotated relative to the scope cap 13A.

The slider 5 is a substantially cylindrical member made of resin, etc. A first end section 4A of the main body 4 is inserted from a first end section 5A of the slider 5. The slider 5 is slidable in a specific range in an axial direction relative to the main body 4.

A slider-fixing section (engaging member) 14 is attached to the first end section 5A in the slider 5. The slider-fixing member 14 fixes the slider 5 to the main body 4. The attached slider-fixing member 14 is positioned between the inner surface of the slider 5 and an outer surface of the main body 4.

The slider-fixing member 14 has: a main body plate 15 having substantially a plate shape; a first engagement section 16 provided to an end section of the first end section 5A; and a second engagement section 17 provided to the end opposite a first engagement section 16. A surface 15A of the slider 5 directed radially inward is flat. A surface 15B of the slider 5 has a first engagement section 16 and a second engagement section 17 where the radial thickness of the first engagement section 16 increases outwardly and the second engagement section 17 is flat.

Engagement projections 16A and 17A directed inwardly in a radial direction of the slider 5 and capable of engaging with the rack teeth 9 and the engagement projection section 9A are provided to the first engagement section 16 and the second engagement section 17. As shown in FIG. 2A, The engagement projection 16A is engaged softly to the engagement projection 16A, i.e., manually slidable on the engagement projection section 9A. A contact projection 16B making contact with the inner surface of the slider 5 is provided on an outer periphery in a radial direction of the first engagement section 16, i.e., opposite the engagement projection 16A. The thickness of the slider-fixing member 14 in FIG. 2A of a minimum degree at the second engagement section 17 of the main body plate 15. The thickness increases at the first engagement section 16 relative to the tilting section 15C. The thickness is of a maximum degree at a position of the contact projection 16B of the first engagement section 16.

FIG. 3A is an enlarged view of an automatic puncture unit 6 and the area therearound shown in FIG. 2A, and FIG. 3B is an enlarged view of the automatic puncture unit 6 and therearound as shown in FIG. 2B. As illustrated in FIGS. 3A and 3B, the automatic puncture unit 6 is attached to a second end section 5B that is opposite the first end section 5A of the slider 5. The basic configuration of the automatic puncture unit 6 is the same as that of a puncture apparatus disclosed in Japanese Patent Application Laid-open No. 2007-68732. That is, the automatic puncture unit 6 is provided with: a hammer 18 making contact with a contacting section 5C provided to the slider 5 when the needle tube 2 is ejected; a retraction state-maintaining member 19 slidable relative to the hammer 18 in an axial direction; a plunger (needle tube-maneuvering section) 20 having the hammer 18 and the retraction state-maintaining member 19 inserted therethrough; a coil spring (ejecting member) 21 disposed on an outer periphery of the plunger 20; an operation switch (operation section) 22 that activates the automatic puncture unit 6; and a protection cover (erroneous movement preventive member) 23 that covers the operation switch 22.

The hammer 18 having a screw formed on the outer periphery thereof can be engaged with a screw thread provided on an inner surface of the plunger 20. A flange 18A is provided on an end section of the hammer 18 at the first end section 5A. Two side walls 18B extending from the end section having the flange 18A to the first end section 5A place the main body 4 therebetween in the slider 5.

The retraction state-maintaining member 19 not having a screw thread on the outer periphery is smoothly slidable in an axial direction in the plunger 20. A flange 19A is provided to an end section of the retraction state-maintaining member 19 at the first end section 5A. A retraction state-maintaining projection section 19B that constitutes a part of the flange 19A further projects outwardly in a radial direction of the slider 5. A loading state, which is explained later, of the retraction state-maintaining projection section 19B engages with an operation switch 22.

A plunger 20 is a substantial cylindrical member having an end section inserted through and freely sliding on the slider 5 in the axial direction thereof. A flange 20A provided at a predetermined position on the outer periphery of the plunger 20 prevents the plunger 20 from moving further forward than a specific length into the slider 5.

A needle tube-fixing member 24 is attached to the other end of the plunger 20. The proximal end of the needle tube 2 passing through the hammer 18, the retraction state-maintaining member 19, and the plunger 20 is fixed to a first end section 24A of the needle tube-fixing member 24. A second end section 24B of the needle tube-fixing member 24 is a substantial cylinder to which an injection needle can be attached. A wire state of stilet 25 extending from the second end section 24B of the needle tube-fixing member 24 is inserted through the needle tube 2 so as to reinforce the needle tube 2 when inserted and to prevent a non-object tissue from entering the needle tube 2. A rear end of the stilet 25 is connected to a stilet knob 26 that is engaged with and fixed at the second end section 24B of the needle tube-fixing member 24.

A spring 21 made of metal, etc., is disposed to surround an outer surface of the plunger 20. A diameter of a component that forms the spring 21 may be determined appropriately based on an ejection force required for automatic puncture. A substantial cylinder spring cover 21A is attached to an outer periphery of the spring 21.

As illustrated in FIG. 3A, an operation switch 22 is a plate member having a center and thereabouts in the longitudinal direction that are supported by a rotation shaft 22A and fixed to the slider 5. A groove state of engagement section 22B that is capable of engaging with a retraction state-maintaining projection section 19B of the retraction state-maintaining member 19 is provided to an end section of the operation switch 22. A spring 27 disposed to the other end section of the operation switch 22 continuously urges the operation switch 22 around the rotation shaft 22A in the counter-clockwise direction in FIG. 2.

A protection cover 23 is a plate member, attached to the slider 5 and is slidable in a specific range of the axial direction, that covers the operation switch 22. The length of the protection cover 23 is set so that one of the end sections 23A continuously enters between the slider-fixing member 14 the inner surface of the slider 5.

Operations in use of the puncture apparatus 1 having the aforementioned configuration are explained as follows with reference to FIGS. 4A to 8B. An endoscope is first inserted into a body cavity of a patient using a commonly known method and subsequently forwarded to an object organ or the vicinity thereof.

Figure 4B:
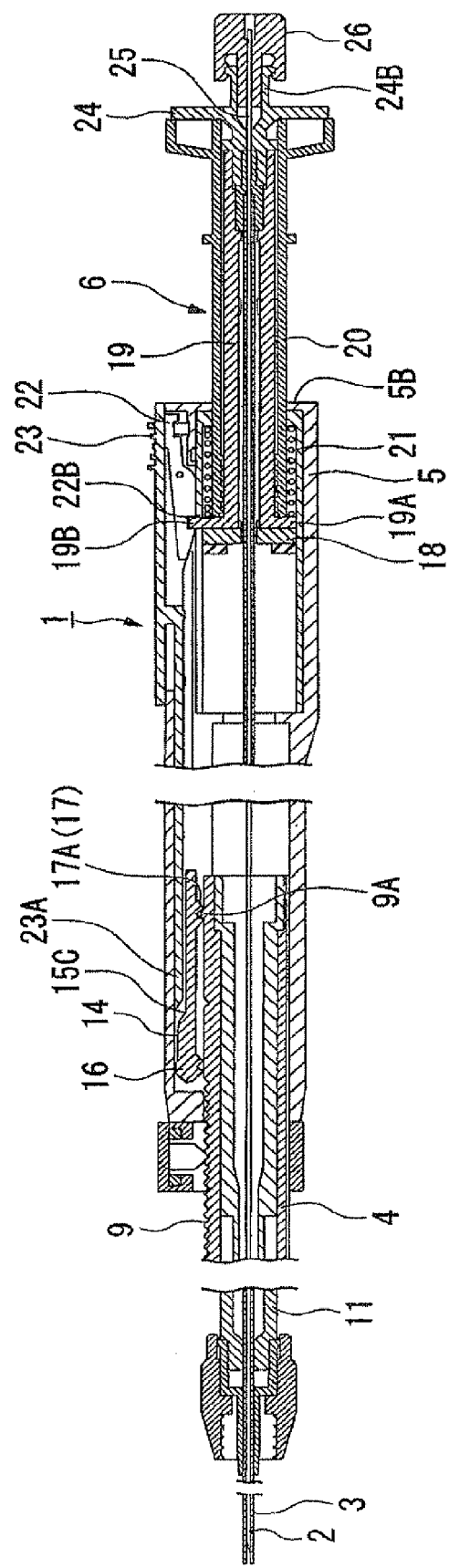
FIG. 4B is a vertical cross-section of the same state.

A user retracts the plunger 20 toward a proximal end. Accordingly, since the hammer 18 and the retraction state-maintaining member 19 along with the plunger 20 move toward their proximal ends as illustrated in FIGS. 4A and 4B, the retracted state of the plunger 20 is maintained by engaging the retraction state-maintaining projection section 19B of the retraction state-maintaining member 19 to the engagement section 22B of the operation switch 22. Since this state of the main body 4 placed between the side walls 18B of the hammer 18 moves toward its proximal end, the correlation between the needle tube 2 and the sheath 3 is maintained.

This operation of shortening the distance between the second end section 5B of the slider 5 and the flange 19A of the retraction state-maintaining member 19 compresses the spring 21, thereby accumulating an ejection force for automatic puncture in the spring 21. Hereinafter this state is referred to a "loading state".

Figure 6A:
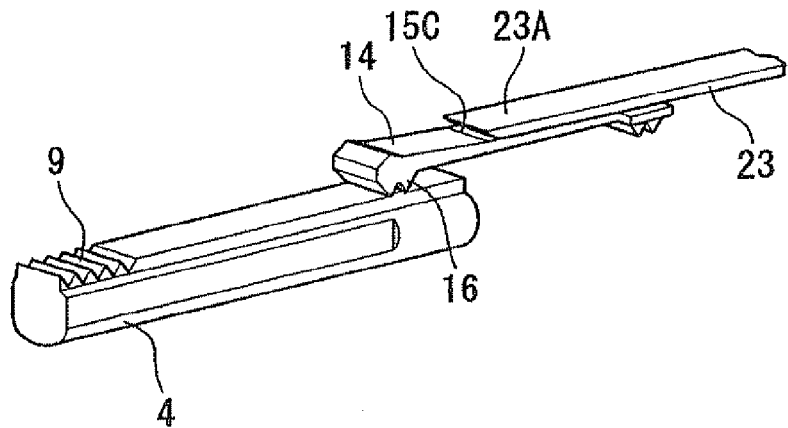
FIGS. 6A to 6C show cooperative movements of a main body, a slider-fixing section, and a protection cover of the puncture apparatus that are linked.
Figure 6B:
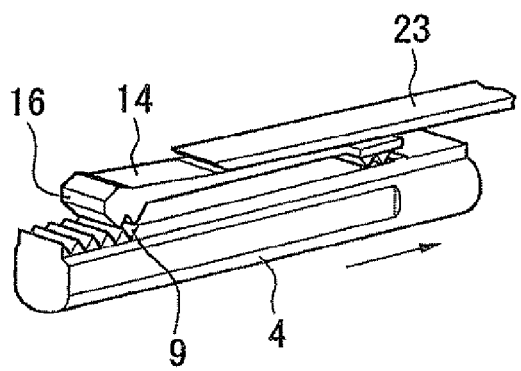

The end section 23A of the protection cover 23 cannot move toward the first engagement section 16 relative to a tilting section 15C of the slider-fixing member 14, since, as illustrated in FIGS. 4B and 6A, the first engagement section 16 of the slider-fixing member 14 does not engage with the rack teeth 9 of the main body. Therefore sliding the protection cover 23 does not allow the operation switch 22 to be exposed for operation. A "click" feeling is conveyed to the user since the engagement projection 17A of the second engagement section 17 of the slider-fixing member 14 engages with the engagement projection section 9A of the main body 4 in a loose fit so that manipulation to the engagement projection section 9A can slide thereof.

The sheath adjuster 11 subsequently extended most from the puncture apparatus 1 and being in the loading state of the automatic puncture unit 6 provides the shortest projection length of the sheath 3. Subsequently inserting the needle tube 2 and the sheath 3 into an operation channel from the forceps port of the endoscope, and fixing the section 13 at the forceps port cause the puncture apparatus 1 to be fixed to the endoscope.

Subsequently untightening the sheath adjuster screw 12 slides the main body 4 relative to the sheath adjuster 11 toward the distal end of the sheath 3, thereby adjusting the projection length of the sheath 3 and exposing the sheath 3 from the distal end of the endoscope.

The user pulls a stilet knob 26 to retract the stilet 25 and connects an injection needle, not shown in the drawings, to the second end section 24B of the needle tube-fixing member 24. Providing negative pressure to the inside of the needle tube 2 facilitates tissue removal. Subsequently, sliding the slider 5 relative to the main body 4 toward the distal end of the needle tube 2 exposes the distal end of the needle tube 2 from the sheath 3. If necessary the needle adjuster 10 may be referred to the sliding distance of the slider 5.

Manual puncture is first attempted for an object tissue, etc., by using the distal end of the exposed needle tube 2. In the case of an unsuccessful manual puncture due to fibrosis of the object tissue, etc., the length of the hammer 18 engaging with the plunger 20 is adjusted, and the projection length of the needle tube 2 from the sheath 3 in an automatic puncture state is set, and then automatic puncture is conducted by activating the automatic puncture unit 6. Since this state of the slider 5 is slid to the distal end of the needle tube 2, as illustrated in the correlations in FIGS. 5B and 6B, the first engagement section 16 of the slider-fixing member 14 is capable of engaging with the rack teeth 9 of the main body 4.

Figure 6C:
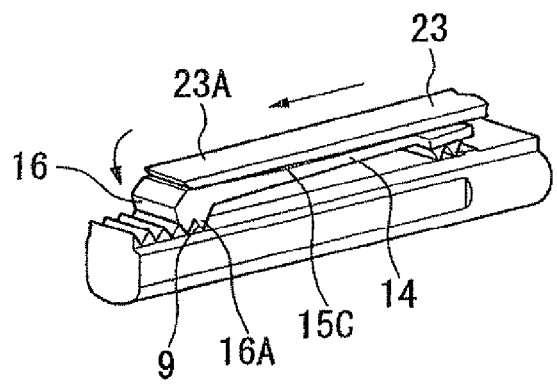
Figure 8A:
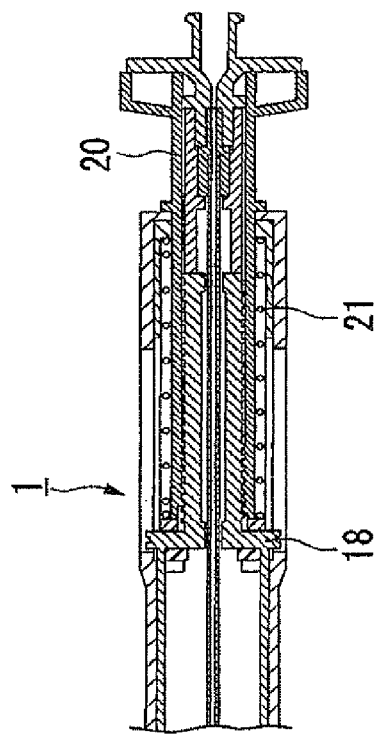
FIG. 8A is a horizontal cross-section of an activated state of the automatic puncture unit of the puncture apparatus.
Figure 8B:
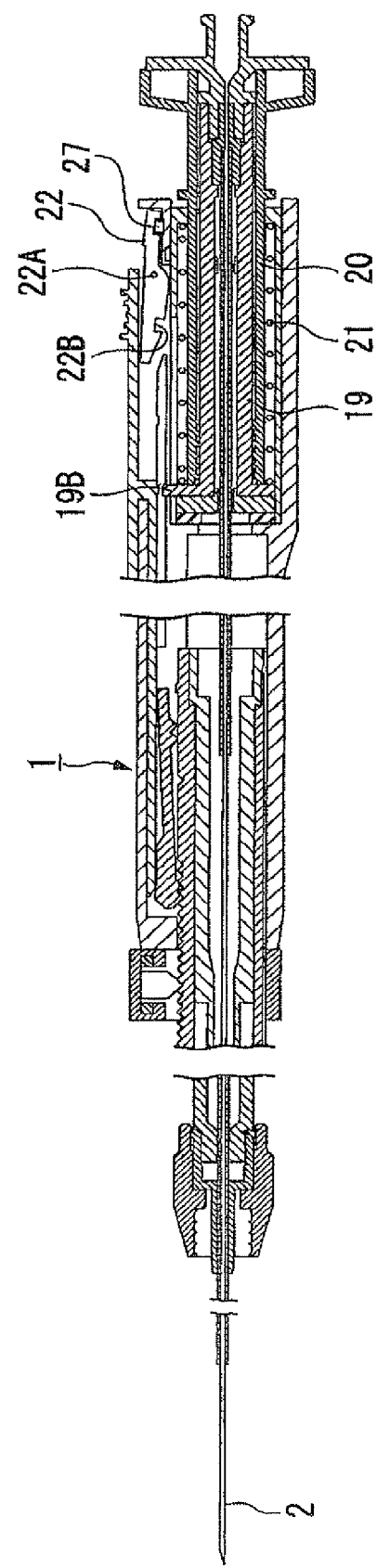
FIG. 8B is a vertical cross-section of the same state.

As illustrated in FIG. 6C, an attempt by the user to slide the protection cover to expose the operation switch 22 moves the first engagement section 16 pushed by the end section 23A by a depth of the rack tooth 9 inwardly with respect to the radial direction of the slider 5, thereby engaging the engagement projection 16A to the rack teeth 9. This results in increasing the distance between the slider-fixing member 14 and the inner surface of the slider 5, thereby allowing the end section 23A of the protection cover 23 to move across the tilting section 15C in the vicinity of the first engagement section 16. The operation switch 22 can be exposed by sliding and retracting the protection cover as illustrated in FIGS. 7A and 7B.

If the user presses the end section having the spring 27 of the operation switch 22, the operation switch 22 rotates around the rotation shaft 22A, and the engagement section 22B moves outwardly with respect to the radial direction of the slider, and thereby the engagement between the engagement section 22B and the retraction state-maintaining projection section 19B is released. This results in the release of the loading state, thereby allowing the ejection force accumulated in the spring 21 to move the hammer 18, the retraction state-maintaining member 19, and the plunger 20 toward their distal ends. The needle tube 2 fixed to the plunger 20 accordingly moves toward the object tissue for automatic puncture.

The mere sliding of the protection cover 23 cannot expose the operation switch 22 in the puncture apparatus 1 according to the above embodiment unless: sliding the slider 5 forward; exposing the distal end of the needle tube 2 from the sheath 3; and achieving the correlation where the rack teeth 9 of the main body 4 can be engaged with the first engagement section 16 of the slider-fixing member 14. Therefore, an unintentional activation of the automatic puncture unit 6 by the user can be prevented since the automatic puncture unit 6 cannot be activated substantially after completion of a manual puncture.

An unintended timing projection of the distal end of the needle tube 2 from the sheath 3 can also be prevented since the engagement projection section 9A provided to the main body loosely engages with the first engagement section 16 of the slider-fixing section or with the engagement projections 16A and 17A of the second engagement section 17 in prior to and subsequent to setting the loading state. Furthermore, the "click" feeling at the time of engagement conveyed to the user facilitates recognition by the user of the engaging state.

A second embodiment of the present invention will be explained next with reference to FIGS. 9A to 10C. A puncture apparatus 31 according to the present embodiment is different from the previously explained puncture apparatus 1 because of a proximal end section of a slider.

Note that elements that are equivalent to the puncture apparatus 1 will be assigned the same reference symbols and redundant explanations thereof will be omitted in each of the following embodiments.

FIG. 9A is an enlarged horizontal cross-section of an automatic picture unit 6 of the puncture apparatus 31 and the area therearound. FIG. 9B is an enlarged vertical cross-section thereof. An end section 32B making contact with a rear end of the spring cover 21A is formed on a proximal end section 32A of the slider 32. A notch 32C is provided in the general vicinity of the outer periphery of the slider 32 of the end section 32B as illustrated in FIGS. 9A and 9B where the thickness of the end section 32B is reduced.

Excessive load applied to the slider 32 by the automatic puncture unit 6 activated multiple times first destroys the end section 32B having decreased strength due to the notch 32C in the puncture apparatus 31 according to the present embodiment. Therefore, the destruction of the end section 32B releases the ejection force accumulated in the spring 21 because the spring 21 extends to its proximal end, i.e., in the direction of the stilet knob 26; thus, the automatic puncture unit 6 is not activated. This results in preventing the destruction of the slider 32, unintentional activation of the automatic puncture unit 6, and projection of the distal end of the needle tube 2.

Also, the spring 21 and the spring cover 21A collide with the flange 20A provided to the plunger 20 upon destruction of the end section 32B. Therefore, the spring 21, etc., will hardly hit the hand or finger of a user manipulating the plunger 20; thus the puncture apparatus 31 can be used safely.

Although an example of the end section 32B explained for the present embodiment has a notch 2C therearound, the notch 32C may be provided only partly in the vicinity of the outer periphery of the slider 32. Also, the notch 32O may be provided on an outer surface of the slider 32.

Figure 10A:
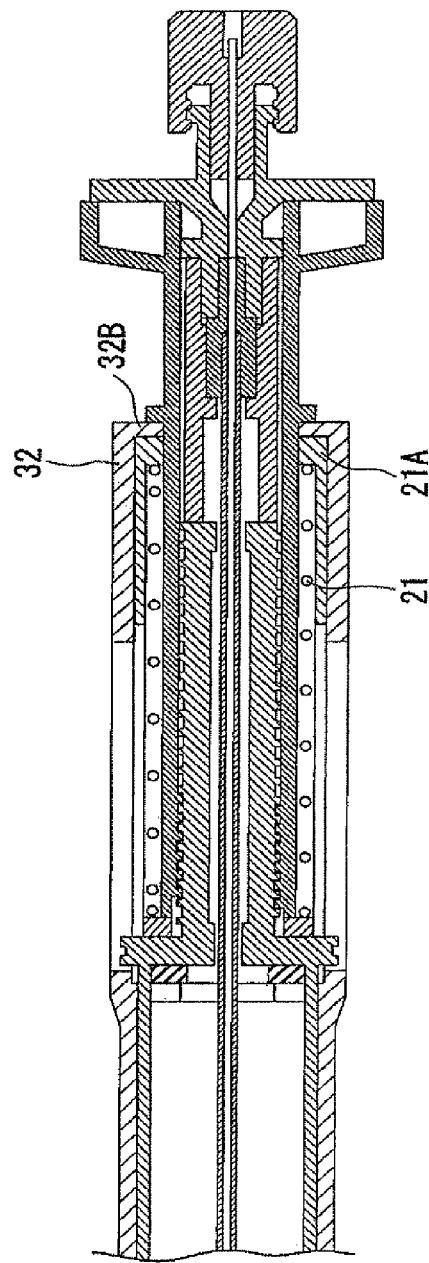
FIG. 10A is an enlarged horizontal cross-view of the automatic puncture unit 6 and the area therearound according to a modified example of the puncture apparatus.
Figure 10B:
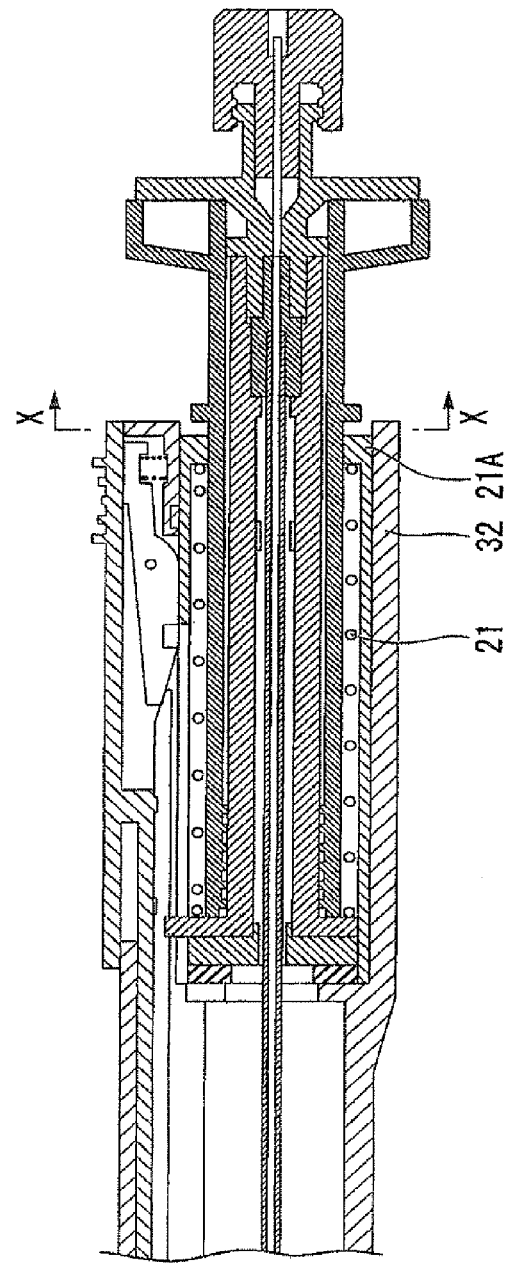
FIG. 10B is an enlarged vertical cross-section.
Figure 10C:
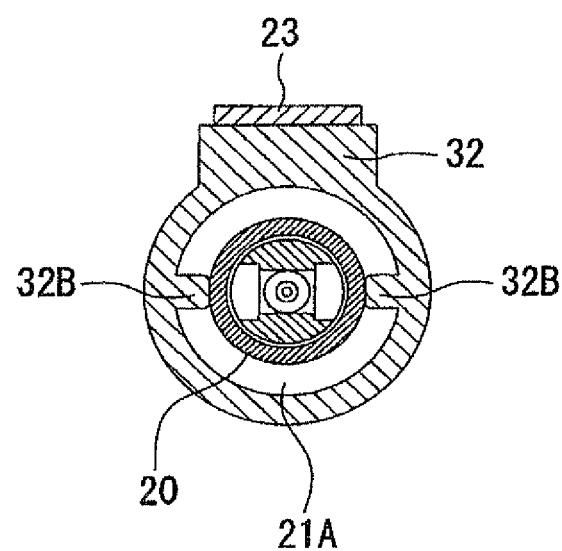
FIG. 10C is a cross-section viewed along X-X line of FIG. 10B.

Furthermore the end section 32B may be provided partly in a circumferential direction of the slider 32 as illustrated in FIGS. 10A to 10C in place of providing the notch 32C. This results in causing only two laterally positioned end sections 32B to support the spring 21 and the spring cover 21A as illustrated in a cross-sectional FIG. 10C. The strength of the end section 32B can therefore be reduced; thus a similar effect as that of the puncture apparatus 31 according to the present embodiment can be obtained.

Vulnerability of the end surfaces associated with load applied to the slider may be determined appropriately in consideration of strength of the spring 21 or durability of the needle tube 2, etc.

A third embodiment of the present invention will be explained next with reference to FIGS. 11A to 12B. A puncture apparatus 41 according to the present embodiment is different from the previously explained puncture apparatus 1 because of a structure that fixes the sheath adjuster. FIGS. 11A to 12B omit the needle tube 2 for the purpose of visibility in these drawings.

Figure 11A:
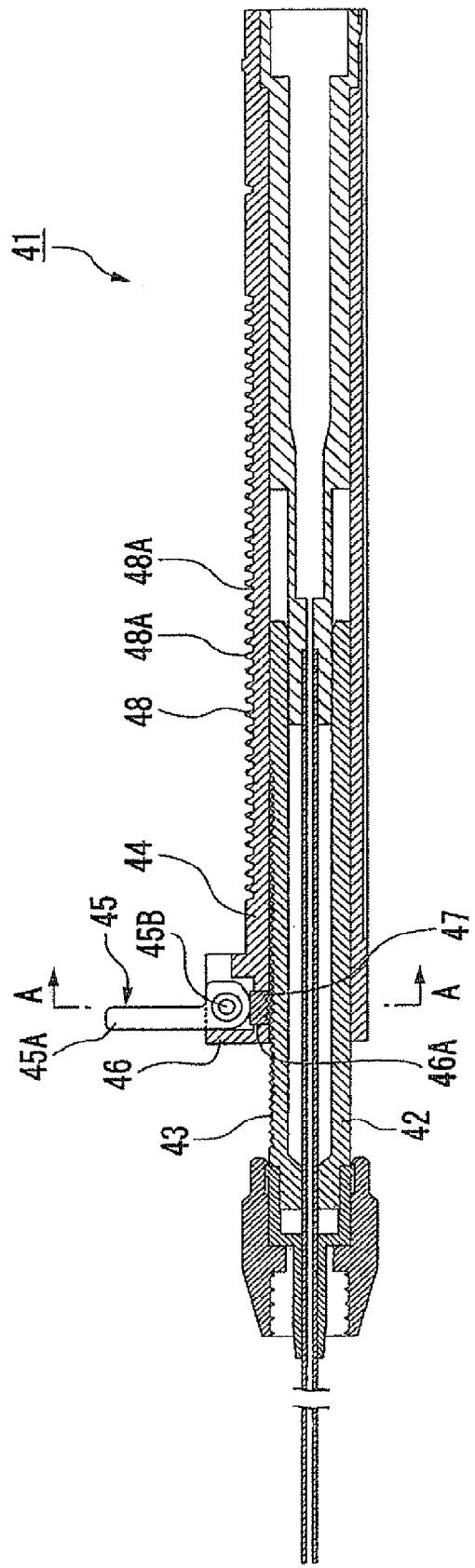
FIG. 11A is an enlarged vertical cross-view in the vicinity of a distal end of the puncture apparatus and therearound according to a third embodiment of the puncture apparatus.
Figure 11B:
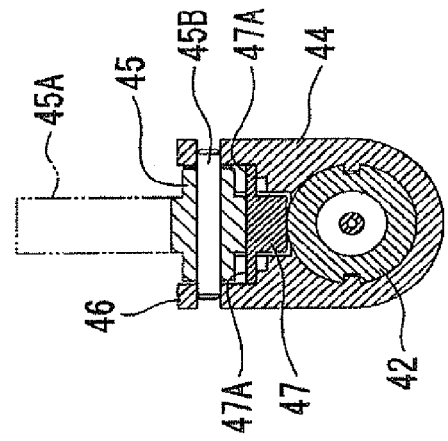
FIG. 11B is a cross-section viewed in A-A line shown in FIG. 11A.

FIG. 11A is an enlarged vertical cross-view in the vicinity of a distal end of the puncture apparatus 41 and the area therearound. FIG. 11B is a cross-section viewed in A-A line shown in FIG. 11A. A plurality of second rack teeth (section to be attached) 43 are provided on an outer periphery of the sheath adjuster 42 of the puncture apparatus 41 in an axial direction. An adjuster lever 45 in place of a sheath adjuster screw is provided to the main body 44. The adjuster lever 45 having a handle 45A at an end thereof is attached to a cylindrical section 46, provided to an end section of the main body 44, by a rotation shaft 45B so that the adjuster lever 45 is rotatable in a specific range.

A bottom section 46A of the cylindrical section 46 has an opening in which an adjuster-fixing member (slider-fixing section) 47 that can engage with second rack teeth 43 is disposed between the adjuster lever 45 and the sheath adjuster 42. As illustrated in FIG. 11B, the adjuster-fixing member 47 is supported by a tongue piece 47A extending in a width direction of the main body 44 in the cylindrical section 46 so that the adjuster-fixing member 47 is separate from the sheath adjuster 42.

The rack teeth 48 each of the main body 44 has a tilting surface having an angle of 60 degrees with respect to the axial line of the main body 44. A horizontal surface 48A for maintaining the thickness of each of the rack teeth 48 is provided to an upper part of each of the rack teeth 48 and to a valley part among the rack teeth 48.

Operations in using the puncture apparatus 41 having the previously explained configuration will be explained. When the handle 45A of the adjuster lever 45 is directed upward as illustrated in FIG. 11A, the sheath adjuster 42 can freely slide in the axial direction of the main body 44 since the adjuster-fixing member 47 is separated from the sheath adjuster 42.

Figure 12A:
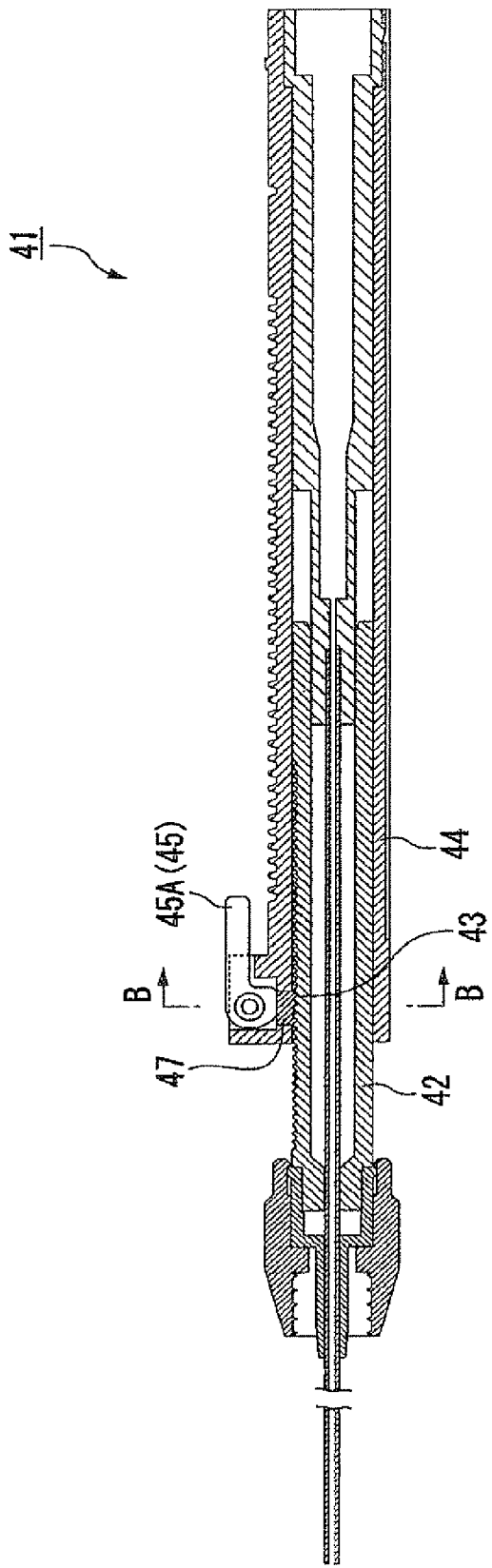
FIG. 12A is an enlarged cross-section showing a fixed state of a sheath adjuster of the puncture apparatus to the main body.
Figure 12B:
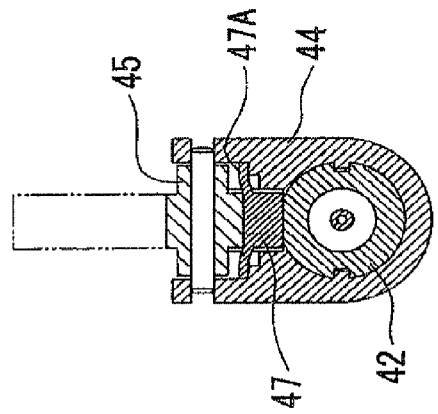
FIG. 12B is a cross-section viewed in B-B line shown in FIG. 12A.

A user upon determining the length of the sheath adjuster 42 rotates the spring cover 21A as illustrated in FIG. 12. Since this state of a lower end of the adjuster lever 45 is positioned below a position illustrated in FIG. 11A, the tongue piece 47A of the adjuster-fixing member 47 bends as illustrated in FIG. 12B; thus, the adjuster-fixing member 47 moves downward. Consequently the adjuster-fixing member 47 engages with the second rack teeth 43 of the sheath adjuster 42; thus, the sheath adjuster 42 is fixed to the main body 44. Readjusting the length of the sheath adjuster 42 necessitates the rotation of the handle 45A upwardly; thereby releasing the engagement between the adjuster-fixing member 47 and the sheath adjuster 42 and allowing the sheath adjuster 42 to slide freely.

In the puncture apparatus 41 according to the present embodiment, the sheath adjuster 42 can be fixed to the main body 44 reliably by a simple operation, i.e., rotating the handle 45A of the adjuster lever 45 causes the adjuster-fixing member 47 to engage with the second rack teeth 43 of the sheath adjuster 42. Therefore a puncture apparatus can be structurally configured to avoid an unintentional slip of the sheath adjuster 42 when a significant impact caused by the activation of the automatic puncture unit 6 is applied to the puncture apparatus 41.

In addition, an incident, e.g., the engagement section 10A of the needle adjuster 10 or the engagement projection 16A of the slider-fixing member 14 overriding the rack teeth 48 and moving forward, will hardly occur even if a significant impact is applied to the slider 5 by the automatic puncture unit 6, since the rack teeth 48 of the main body 44 project at a steep angle, e.g., substantially 60 degrees. Therefore the projection length of the automatic puncture unit 6 can be controlled reliably.

Figure 13A:
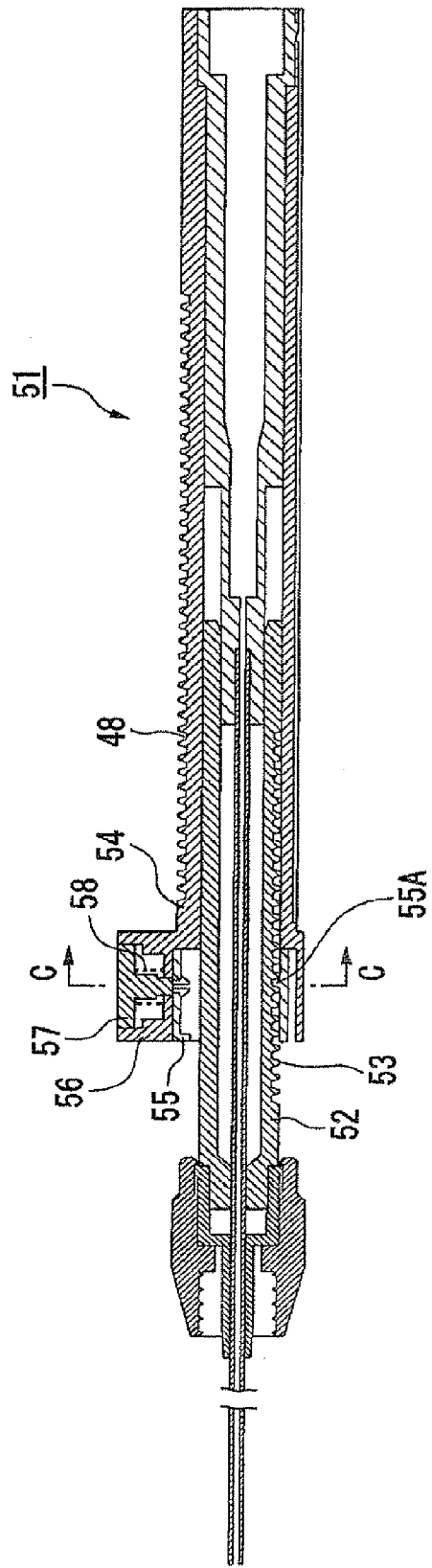
FIG. 13A is an enlarged vertical cross-view in the vicinity of a distal end of the puncture apparatus and the area therearound according to a fourth embodiment of the present invention.

A fourth embodiment of the present invention will be explained next with reference to FIGS. 13A to 14. A puncture apparatus 51 according to the present embodiment is different from the previously explained puncture apparatus 1 according to the fourth embodiment because of a structure that fixes the sheath adjuster. FIGS. 13 to 14 each omits the needle tube 2 for visibility of these drawings.

FIG. 13A is an enlarged vertical cross-view in the vicinity of a distal end of the puncture apparatus 51 and the area therearound. FIG. 11B is a cross-section viewed in B-b line shown in FIG. 13A. The sheath adjuster 52 of the puncture apparatus 51 is inserted into a main body 54 so that second rack teeth 53 project in a direction opposite the rack teeth 48 of the main body 54. A substantial ring-shaped adjuster-fixing member 55 having an engagement section 55A capable of engaging with the second rack teeth 53 is disposed in the vicinity of the end section of the main body 54. The sheath adjuster 52 is inserted into the adjuster-fixing member 55.

A substantially cylindrical section 56 is provided further onto the adjuster-fixing member 55 provided on the outer periphery of the main body 54. A button 57 is disposed in the cylindrical section 56. A spring 58 disposed between the button 57 and a bottom surface of the cylindrical section 56 continuously urges the button 57 outwardly in a radial direction of the main body 54. The bottom end of the button 57 penetrating the bottom surface of the cylindrical section 56 and the adjuster-fixing member 55 locks the adjuster-fixing member 55.

Figure 13B:
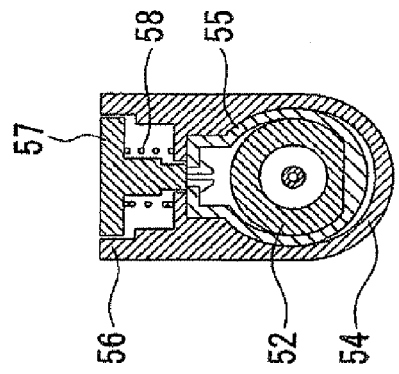
FIG. 13B is a cross-section viewed in C-C line shown in FIG. 13A.
Figure 14:
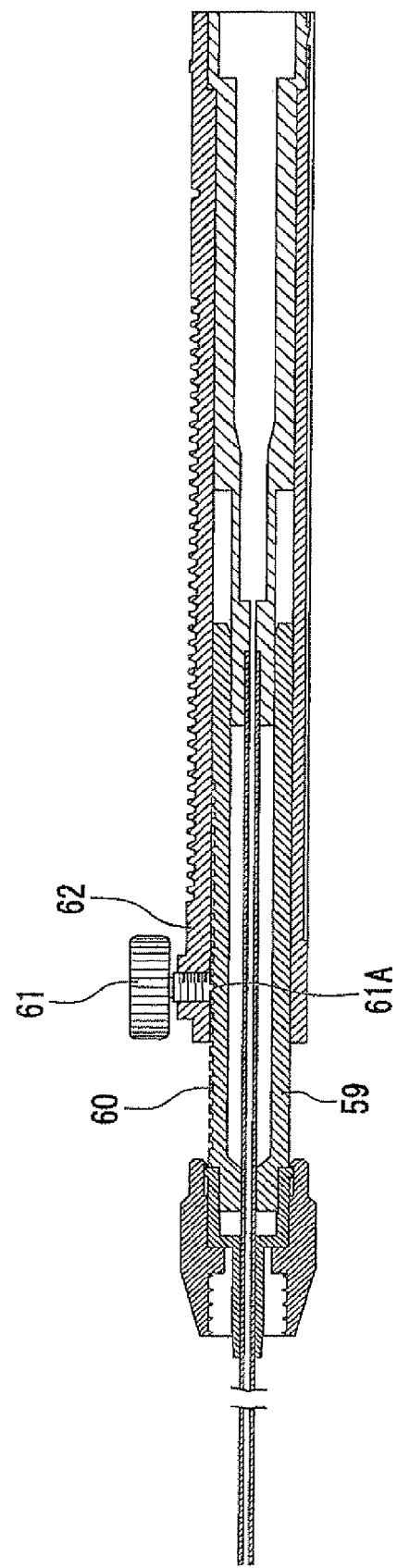
FIG. 14 is an enlarged cross-section in the vicinity of a distal end in a modified example of the puncture apparatus.

Since the button 57 is urged upward by the spring 58 in unpressed state as illustrated in FIG. 13A, the adjuster-fixing member 55 engaged by the button 57 is also pulled upward as illustrated in FIG. 13B. The correlation between the sheath adjuster 52 and the main body 54 is fixed since the engagement section 55A of this state of adjuster-fixing member 55 engages with the second rack teeth 53 of the sheath adjuster 52.

The button 57 is pushed for adjusting the length of the sheath adjuster 52 projecting from the main body 54. Accordingly, the adjuster-fixing member 55 locked by the button 57 moves downward as illustrated in FIG. 13A and releasing the engagement of the engagement section 55A with the second rack teeth 53; therefore, the sheath adjuster 52 can slide freely relative to the main body 54.

In the puncture apparatus 51 according to the present embodiment, the sheath adjuster 52 can be fixed to the main body 54 reliably by a simple operation similarly to that of the puncture apparatus 41 according to the third embodiment.

A structure for fixing the sheath adjuster to the main body is not limited to those of the previously explained third and fourth embodiments. A modified example as illustrated in FIG. 14 can obtain an effect substantially the same in which recessed portions 60 to be fixed are provided at a specific interval in an axial direction of the sheath adjuster 59; and an engaging section 61A (slider-fixing section), that engages with the recessed portion 60, is formed on a bottom end of the sheath adjuster screw 61 that is attached to the main body 62.

A puncture apparatus 71 according to a fifth embodiment of the present invention will be explained next with reference to FIGS. 15A to 16. The puncture apparatus 71 according to the present embodiment is different from the puncture apparatus 1 according to the previously explained first embodiment because a stopper is disposed in place of a protection cover.

Figure 15A:
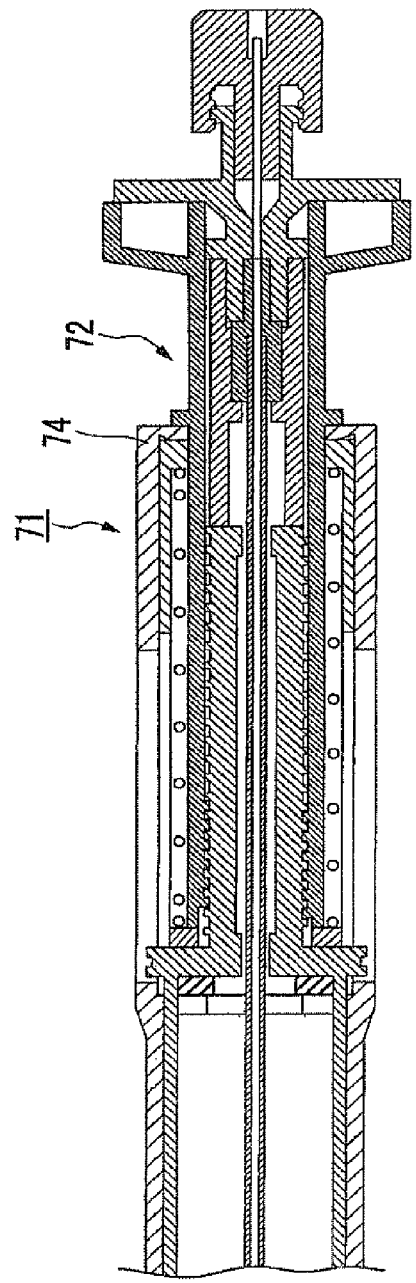
FIG. 15A is an enlarged horizontal cross-section of an automatic picture unit of the puncture apparatus according to a fifth embodiment of the present invention.
Figure 15B:
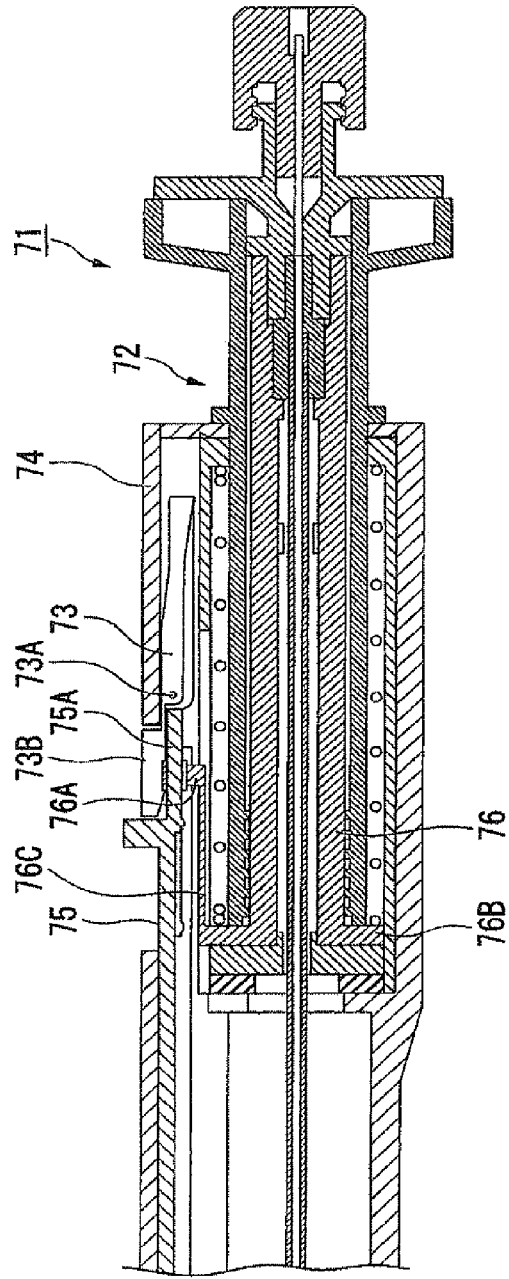
FIG. 15B is an enlarged vertical cross-section thereof.

FIG. 15A is an enlarged horizontal cross-section of an automatic picture unit 72 of the puncture apparatus 71. FIG. 15B is an enlarged vertical cross-section thereof. As illustrated in FIG. 15B, an operation switch 73 of the puncture apparatus 71 is supported by a rotation shaft 73A in the slider 74 similarly to the operation switch 22 according to the first embodiment. An end section 75A of a stopper 75 that prevents erroneous movement of the operation switch 73 is interposed between the end section 73B of the distal end of the operation switch 73 and the automatic puncture unit 72. The stopper 75, which is a plate member, is attached to the slider 74 so that the stopper 75 is capable of sliding in an axial direction of the slider 74. The other end section 75B of the stopper 75 enters between the slider-fixing member 14 and the inner surface of the slider 74 continuously similarly to the end section 23A of the protection cover according to the first embodiment.

A retraction state-maintaining projection section 76A of a retraction state-maintaining member 76 of the automatic puncture unit 72 is provided to a distal end of a retraction state-maintaining tongue piece 76C extending from the flange 76B toward its proximal end. That is, the retraction state-maintaining projection section 76A is positioned close to the rear end of the slider 74 relative to the flange 76B.

Operations in using the puncture apparatus 71 having the previously explained configuration will be explained.

The stopper 75 blocked by the slider-fixing member 14 cannot slide forward similarly to the protection cover 23 according to the first embodiment until the user slides the slider 74 forward to a correlational position where the rack teeth 9 of the main body 4 can engage with the first engagement section 16 of the slider-fixing member 14. Therefore, the end section 75A of the stopper 75 cannot be retracted from between the end section 73B of the distal end of the operation switch 73 and the automatic puncture unit 72. The end section 73B cannot be pressed, and thus the automatic puncture unit 6 cannot be activated.

Figure 16:
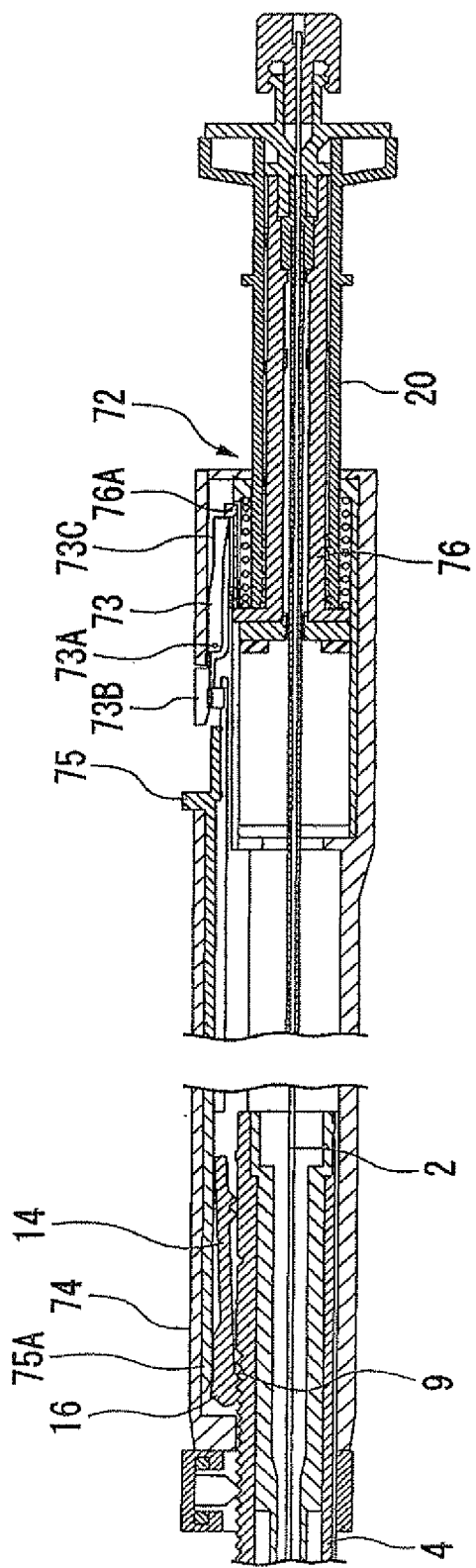
FIG. 16 is a cross-section showing the loading state of the automatic puncture unit of the puncture apparatus and a slid state of a slider forward with respect to a puncture direction.

FIG. 16 is a view showing the loading state of the automatic puncture unit 72 and a state of a slider 74 having been slid forward with respect to a puncture direction. The retraction state-maintaining projection section 76A of the retraction state-maintaining member 76 engaging with the end section 73C of the rear end of the operation switch 73 maintains the retracted state of the plunger 20 in the puncture apparatus 71.

In this state of correlation, the rack teeth 9 of the main body 4 can engage with the first engagement section 16 of the slider-fixing member 14. Therefore, the end section 75A of the stopper 75 slidable in the vicinity of the first engagement section 16 can be retracted from between the operation switch 73 and the automatic puncture unit 72 by sliding the stopper 75 as illustrated in FIG. 16.

The operation switch 73 rotates around the rotation shaft 73A upon the user having pushed the end section 73B of the operation switch 73 after retracting the stopper 75. The end section 73C moves upward accordingly, and the engagement between the end section 73C and the retraction state-maintaining projection section 76A is released. Thus, the needle tube 2 is projected for automatic puncture.

The stopper 75 cannot be retracted from beneath the operation switch 73 in the puncture apparatus 71 according to the present embodiment unless the slider 74 is slid forward and the distal end of the needle tube 2 is exposed. Therefore, an unintentional activation of the automatic puncture unit 72 by the user can be prevented since the automatic puncture unit 72 cannot be activated substantially after completion of manual puncture similarly to the first embodiment.

A sixth embodiment of the present invention will be explained next with reference to FIGS. 17A and 17B. A puncture apparatus 81 according to the present embodiment is different from the previously explained puncture apparatus 1 because of a structure in an section to be attached with an endoscope.

Figure 17A:
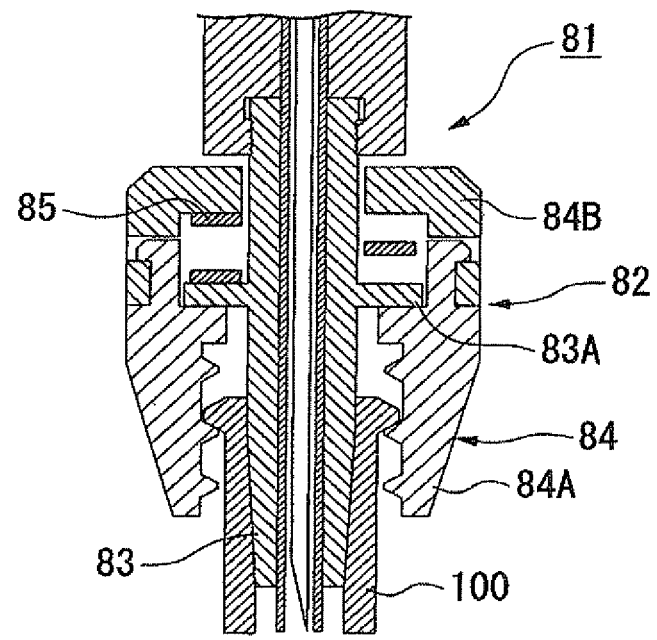
FIG. 17A is an enlarged cross-section of an section of the puncture apparatus that is attached to an endoscope according to a sixth embodiment of the present invention.

FIG. 17A is an enlarged cross-section of a section 13 of the puncture apparatus 81 that is to be attached with an endoscope. A flange 83A is provided in the middle of the axial direction of a scope cap 83 according to the present embodiment. The cap screw 84 is constituted by a first member 84A provided at its distal end having a screw thread; and a second end section 84B provided at its rear end. The cap screw 84 is attached rotatively to the scope cap 83 so that the flange 83A is placed between the first member 84A and the second end section 84B. A plate spring 85 disposed between the flange 83A and the second end section 84B urges the scope cap 83 toward its distal end.

As illustrated in FIG. 17A, the scope cap 83 urged by the plate spring 85 makes close contact to the forceps port 100 upon attaching the section 13 to the forceps port 100 of the endoscope.

The puncture apparatus 81 according to the present embodiment can be attached to the endoscope in a more desirable state since close contact between the forceps port 100 and the scope cap 83 can be obtained by the force urged by the plate spring 85.

Since the flange 83A of the scope cap 83 pressed by the plate spring 85 continuously makes contact to the first member 84A of the cap screw 84, rattling, etc., can be prevented when attached to the endoscope.

Figure 17B:
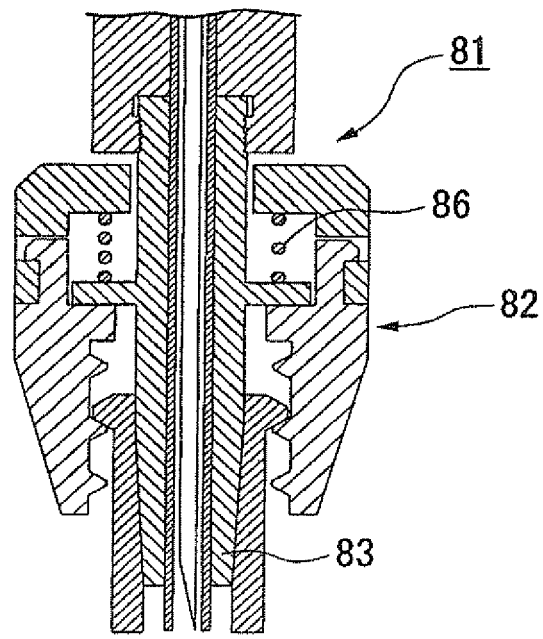
FIG. 17B is an enlarged cross-section of the section of the puncture apparatus that is attached to the endoscope according to a modified example of the puncture apparatus.

In addition to the present embodiment using the plate spring 85, a similar effect can be obtained by disposing a coil spring 86 in place of the plate spring 85 as illustrated in FIG. 17B showing a modified example.

Although the present invention has been described with respect to its preferred embodiments, the present invention is not limited to the embodiments described above. The configuration of the present invention allows for addition, omission, substitution and further modification without departing from the spirit and scope of the present invention.

Figure 18A:
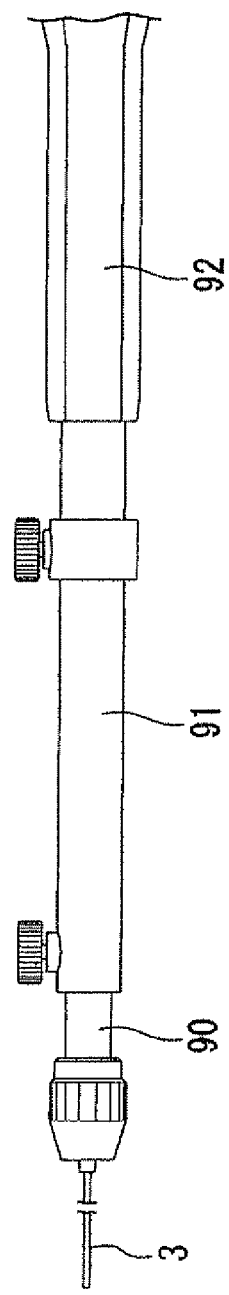
FIGS. 18A and 18B are views showing a puncture apparatus according to a modified example of the present invention.
Figure 18B:
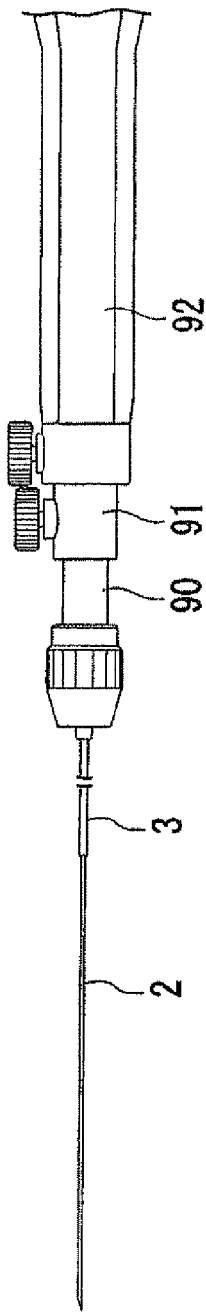

For example, the present invention is not limited to the previously explained structure in which the sheath adjuster and the slider each are slidable in a specific range in axial directions relative to the main body. For further example, a puncture apparatus may be configured so that a sheath adjuster 90 is substantially fully housed in the main body 91; and a main body 91 is fully housed in a slider 92 as illustrated in the modified examples of FIGS. 18a and 18B.

In addition, an object tissue or an organ that is to undergo an operation by the puncture apparatus may not be limited to the pancreas of the previously explained embodiments. The present invention can be used for manipulation conducted for any tissue or organ that will be difficult to remove due to fibrosis.

The present invention is not limited to the above descriptions but is limited only by the appended claims.

What is claimed is:

1. A puncture apparatus with an automatic puncture function, comprising:
    a hollow needle tube;
    a flexible sheath having the needle tube inserted therethrough;
    a main body having one of the ends of the sheath fixed thereto;
    a slider attached to one of the ends of the main body, the slider being capable of sliding in an axial direction relative to the main body, the slider being configured to be capable of adjusting a position of the needle tube relative to the sheath by sliding the slider relative to the main body,
    an engaging member having a portion for releasably engaging with a corresponding portion of the main body such that when the portion of the engaging member is engaged with the corresponding portion of the main body, relative movement between the slider and main body is restricted;
    a needle tube-maneuvering section, attached to one of the ends of the slider, capable of sliding in an axial direction relative to the slider, the needle tube-maneuvering section having a proximal end section of the needle tube fixed thereto;
    a retraction state-maintaining member for maintaining the needle tube-maneuvering section in a retracted state toward the proximal end section;
    an ejecting member provided in the needle tube-maneuvering section, an ejection force for projecting the needle tube-maneuvering section toward a distal end of the main body being accumulated in the needle tube-maneuvering section when the needle tube-maneuvering section is in the retracted state;
    an operation section engaged with the retraction state-maintaining member for releasing the ejection force when the operation section is released from engagement with the retraction state-maintaining member to project the needle tube-maneuvering section toward the distal end of the main body; and
    an unintentional operation preventive mechanism comprising a protection cover movable between a first position covering the operation section and a second position exposing the operation section, the unintentional operation preventive mechanism further having a protection cover motion restriction member engageable with the portion of the engaging member, wherein the unintentional operation preventive mechanism is configured such that it cannot be actuated to expose the operation section unless:
    the slider is moved relative to the main body to expose a distal end of the needle tube from the sheath; and
    the portion of the engaging member is engaged with the corresponding portion of the main body to restrict relative movement between the slider and the main body.

2. The puncture apparatus with an automatic puncture function according to claim 1, wherein:

the portion of the engaging member comprises an engagement projection at a first end section, the engagement projection being able to engage with the corresponding portion of the main body.

3. The puncture apparatus with an automatic puncture function according to claim 2, wherein the corresponding portion of the main body comprises one or more rack teeth.

4. The puncture apparatus with an automatic puncture function according to claim 3, wherein the one or more rack teeth comprises a plurality of rack teeth arranged in the axial direction, each having a tilting surface having an angle of 45 degrees or steeper relative to the axial direction.

5. The puncture apparatus with an automatic puncture function according to claim 1, wherein the engaging member is an interposed member that is interposed between the operation section and the slider.

6. The puncture apparatus with an automatic puncture function according to claim 1, wherein:

the ejecting member is pressed between a front end of the needle tube-maneuvering section and a rear end of the slider;

the rear end of the slider is configured such that a strength of the rear end of the slider is decreased; and an excessive load applied to the slider by an automatic puncture unit first destroys the rear end of the slider thereby releasing the ejection force without projecting the needle tube.

7. The puncture apparatus with an automatic puncture function according to claim 1, wherein the slider includes a first slider and a second slider, the first slider is attached to one of the ends of the main body, the first slider is capable of sliding in the axial direction relative to the main body, the sheath is inserted through the first slider;

the second slider is attached to a second end section of the main body, the second slider is capable of sliding in the axial direction relative to the main body;

the needle tube-maneuvering section is attached to one of the ends of the second slider, capable of sliding in the axial direction relative to the second slider;

the first slider has a plurality of sections to be fixed, the main body has a slider-fixing section that can be engaged with the sections to be fixed, and a predetermined and fixed correlation between the first slider and the main body is obtained by engaging the sections to be fixed with the slider-fixing section.

8. The puncture apparatus with an automatic puncture function according to claim 7, wherein the sections to be fixed are rack teeth each having a tilting surface at an angle of 45 degrees or more relative to the axial line of the main body.

* * * * *